United States Patent
Sabsabi et al.

[11] Patent Number: 6,008,897
[45] Date of Patent: Dec. 28, 1999

[54] METHOD AND APPARATUS FOR MATERIALS ANALYSIS BY ENHANCED LASER INDUCED PLASMA SPECTROSCOPY

[75] Inventors: Mohamad Sabsabi, Boucherville; Paolo Cielo, Montréal; Louis St-Onge, Côte St-Luc, all of Canada

[73] Assignee: National Research Council of Canada, Ottawa, Canada

[21] Appl. No.: 09/232,722

[22] Filed: Jan. 19, 1999

[51] Int. Cl.[6] ................................................. G01N 21/63
[52] U.S. Cl. ............................................................ 356/318
[58] Field of Search ..................................... 356/317, 318

[56] References Cited

FOREIGN PATENT DOCUMENTS

| | | | |
|---|---|---|---|
| 62-85847 | 4/1987 | Japan | 356/318 |
| 62-188919 | 8/1987 | Japan | 356/318 |
| 1-321340 | 12/1989 | Japan | 356/318 |
| 6-241999 | 9/1994 | Japan | 356/318 |

OTHER PUBLICATIONS

Briggs et al., Direct Reading Laser Spectrometer, Western Electric Technical Digest, No. 35, Jul. 1974, pp. 9 and 10.

*Primary Examiner*—F. L. Evans
*Attorney, Agent, or Firm*—Juliusz Szereszewski

[57] ABSTRACT

A method and apparatus is disclosed for enhanced laser-induced plasma spectroscopic analysis of unknown heterogeneous materials. The apparatus has high power pulsed lasers with their beams focused on the material, typically two colinear lasers providing two pulses in the ultraviolet and in the near infrared spectral area. The first laser pulse vaporizes a small volume at the surface of the material and produces a plasma which is subsequently enhanced by the second laser pulse. The optical emission of the plasma is analyzed with a colinear optical spectrometer. The pulsed spectrum is detected by a gated photodiode array detector or by an array of photomultipliers each individually positioned to detect a line emission representative of a given element present in the material. The combination of the two laser pulses, appropriately synchronized, provides a plasma emission that is significantly stronger than a single laser pulse of the combined energy of the two pulses.

16 Claims, 4 Drawing Sheets

METHOD AND APPARATUS FOR MATERIALS ANALYSIS BY ENHANCED LASER INDUCED PLASMA SPECTROSCOPY

BACKGROUND OF THE INVENTION

1. Field of the Invention

This invention relates to a transient, rapid spectroscopic method for analysis of unknown heterogeneous materials by plasma spectroscopy.

2. Related Art

Most analytical techniques used in industry require taking samples to the laboratory, to be analyzed by time consuming procedures involving instrumentation such as Auger and mass spectrometers, EDS, liquid or gas chromatography, graphite furnace atomic absorption spectroscopy or inductively coupled plasma optical emission spectrometry. Faster in-situ methods such as spark-discharge optical spectrometry are only applicable to electrically conductive materials, while X-ray backscattering probes are limited in sensitivity.

An emerging method, laser induced plasma spectroscopy, promises to provide rapid, in-situ compositional analysis of a variety of materials in hostile environments and at a distance. Basically, this method includes focusing a high power pulsed laser on the material, thus vaporizing and ionizing a small volume of the material to produce a plasma having an elemental composition which is representative of the composition of the material. The optical emission of the plasma is analyzed with an optical spectrometer to obtain its atomic composition. This method has been applied to a variety of materials and industrial environments, as exemplified in the following documents.

U.S. Pat. No. 4,645,342 in the name of Tanimoto et al. describes a probe for spectroscopic analysis of steel including focusing an infrared laser pulse on the steel material and collecting, at an angle of 16 degrees or more, the light emitted by the irradiated surface spot, such light being spectrally analyzed. The continuous spectral background is subtracted to obtain the net intensity of preset spectral lines representative of given elements, and the intensity of said spectral lines is related to the concentration of said elements in the steel material. The probe includes a single laser pulse not collinear with the collecting optics.

U.S. Pat. No. 4,986,658 to Kim describes a probe for molten metal analysis by laser induced plasma spectroscopy. The probe contains a high-power laser producing a pulse having a triangular pulse waveshape. When the probe head is immersed in the molten metal, the pulsed laser beam vaporizes a portion of the molten metal to produce a plasma having an elemental composition representative of the molten metal composition. Within the probe, there is provided a pair of spectrographs each having a diffraction grating coupled to a gated intensified photodiode array. The spectroscopic atomic emission of the plasma is analyzed and detected for two separate time windows during the life of the plasma using two spectrometers in parallel. The first time window analyzes the plasma plume before it reaches thermal equilibrium shortly after the termination of the laser pulse, typically 10 nanoseconds long, to detect line reversals caused by absorption of radiation emitted by the hotter inner portion of the plasma plume by relatively cooler outer portions of the plasma plume. Thereafter, after the plasma has reached thermal equilibrium, typically after 1 microsecond, a second time window analyzes the more conventional line emissions from the optically emissive plasma. The spectra obtained during either the first or the second time window, or a combination of both, can be used to infer the atomic composition of the molten metal. In this case the vaporizing laser beam and collecting optics are collinear, but only a single laser pulse is used to vaporize the molten metal surface.

U.S. Pat. No. 5,042,947 to Potzschke et al. describes an application of laser induced plasma spectroscopy for the sorting of solid metal particles, namely shredder scrap from automotive recycling processes. Multiple laser pulses are used to clean the surface from impurities, and up to 30 particles per second can thus be sorted depending on the resulting composition, typically aluminum, zinc, copper, lead and steel. Because the purpose is sorting rather than precise compositional analysis, a relatively low precision and sensitivity can be accepted. A single laser pulse is used to produce each laser spark.

U.S. Pat. No. 5,379,103 to Zigler describes a mobile laboratory for in-situ detection of organic and heavy metal pollutants in ground water. Pulsed laser energy is delivered via fiber optic media to create a laser spark on a remotely located analysis sample. The system operates in two modes, one being based on laser induced plasma spectroscopy and the other on laser induced fluorescence. In the first operational mode, the laser beam guided by fiber optics is focused by a lens on the sample to generate a plasma. The emitted spectrum is analyzed and used to detect heavy metals. In the second mode the focusing laser energy is removed allowing the laser beam via fiber optics to irradiate the sample, so that organic molecules with an aromatic structure emit absorbed ultraviolet energy as fluorescence. The emitted fluorescence light is transmitted via fiber optic media for further analysis. The measured wavelength and time characteristics of the emitted fluorescence can be compared against predetermined characteristics to identify the organic substances in the analysis sample. Again, only single laser pulses are used to analyze pollutants in ground water.

U.S. Pat. No. 5,757,484 by Miles et al. describes a subsurface soil contaminant identification system using a cone penetrometer and based on laser induced breakdown spectrometry. An optical fiber link is used to couple the transmitted and collected beams through the penetrometer to the subsurface soil region to be analyzed. In all of the above patents, single laser pulses are used to vaporize, ionize and excite a portion of the material to be analyzed by laser induced plasma emission spectroscopy.

Piepmeier et al., Anal. Chem. 41, 700 (1969), discuss their work on multiple laser pulses for time and spatially resolved spectrometric observations of laser generated plumes from the surface of a solid aluminum alloy. The laser pulse sequences are random and cannot be controlled, therefore this work does not offer much assistance in quantitative spectrometric analysis.

Two temporally close sparks induced by two collinear lasers are used by Cremers et al. in U.S. Pat. No. 4,925,307 for the spectrochemical analysis of liquids. The laser light is not significantly absorbed by the sample so that the sparks occur in the volume inside the liquid. The spark produced by the first laser pulse produces a bubble in the liquid which stays in the gaseous state for hundreds of microseconds after the first spark has decayed, so that the second laser pulse, fired typically 18 microseconds after the first pulse, will produce a second spark within the gaseous bubble. The spark generated inside the cavity has excitation characteristics close to those of a non-ionized air spark. Due to the much lower density of the gas compared to the liquid, the temperature of the second spark, produced within the gas bubble, is much higher than the temperature of the first spark produced within the liquid. The emission spectrum of the second spark, detected by a spectrometer oriented at 90 degrees from the laser beam axis, is thus much more intense and exhibits reduced line widths compared to the first spark, so that a much increased detectability of the atomic species is obtained by sampling the bubble with the second laser spark. This approach is convenient to analyze relatively transparent liquids so that the first spark is produced in the bulk of the liquid, while the second spark is obtained after a convenient period of time, typically 18 microseconds, has elapsed so that the gas bubble produced by the first pulse has had the time to expand and stabilize. During this period of time the atomic or molecular components in the gas bubble become de-excited and cool down, for optimal line width and detectability. The second pulse thus substantially re-excites a relatively cool gas within a liquid-surrounded bubble.

SUMMARY OF THE INVENTION

It is an object of this invention to provide a method and apparatus for in-situ transient spectroscopic analysis of substantially opaque heterogeneous materials, which provides enhanced emission and detectability as compared to the prior art and which provides an accurate, relatively quick, non-invasive and reproducible indication of the concentration of the sought elements or components of the material.

It is a further object of the invention to provide a signal, indicative of the concentration, that is strong, reliable and repetitive in a wide variety of industrial or hostile environments.

The present invention provides a method and apparatus for a reliable analysis of the surface of a material by using two, preferably colinear laser pulses, temporally spaced by a predetermined time period that is selected to be not long enough to let the plasma spark produced by the first laser pulse to become de-excited. The second pulse, of a wavelength that is efficiently absorbed by the plasma, is thus absorbed by the portion of the plasma spark which faces the incoming laser beams as well as the collection optics of the analyzing spectrometer that is preferably colinear with the two laser beams.

Consequently, the hot outer portion of the plasma spark produced by the second laser pulse irradiates directly into the spectrometer optics without shading, while thermal conduction losses from the hottest portion of the plasma to the surface of the much denser opaque material will be minimized. Furthermore, the temperature distribution across the plasma is more homogeneous for better emission efficiency. The result of the second laser pulse is a plasma spark of high, uniform and sustained temperature and emissivity, so that one can record a plasma emission signal which is significantly stronger than a signal that would be obtained with a single laser pulse having the combined energy of the two pulses.

In one aspect of the invention, there is provided an apparatus for laser-induced spectroscopic analysis of a heterogeneous material, the apparatus comprising:

means for emitting two sequential laser pulses temporally spaced by a predetermined time period, means for focusing the pulses on the surface of said material to generate an enhanced plasma emitting an optical radiation containing radiation which is representative of a selected component of said heterogeneous material, means for measuring the optical radiation of the enhanced plasma after the second laser pulse, and data processing means for determining the concentration of the component in the material.

The emitting means are preferably two lasers disposed such that their optical paths are substantially colinear. A small deviation from the colinearity is acceptable. Alternatively, the two pulses may be generated by a single laser.

The measuring means, e.g. a spectrometer, is preferably disposed substantially colinearly with the optical path of the laser beams.

In another aspect of the invention, there is provided a method for spectroscopic analysis of a heterogeneous material, the method comprising:

a) directing a first single high intensity laser pulse at the surface of said material to generate an ionized plasma, b) waiting a time period that is shorter than sufficient for said plasma to lose its ionization, then c) directing a second single high intensity laser pulse at the plasma generated by the first pulse, said second pulse being of a wavelength to enable at least partial absorption of the energy of said second pulse by said plasma and to create an enhanced plasma containing radiation which is representative of a selected component present in the material, d) measuring the intensity of the radiation of the enhanced plasma, and e) determining the concentration of said selected component in said material as a function of the intensity of the radiation.

Typically, the predetermined time period between the two pulses is between about 0.1 and about 5 microseconds. The time spacing is dependent on the type of material analyzed and can usually be determined experimentally.

BRIEF DESCRIPTION OF THE DRAWINGS

The objects, features and advantages of the present invention will become apparent from the following detailed description of the invention in conjunction with the drawings in which.

DETAILED DESCRIPTION OF THE PREFERRED EMBODIMENTS

Figure 1:
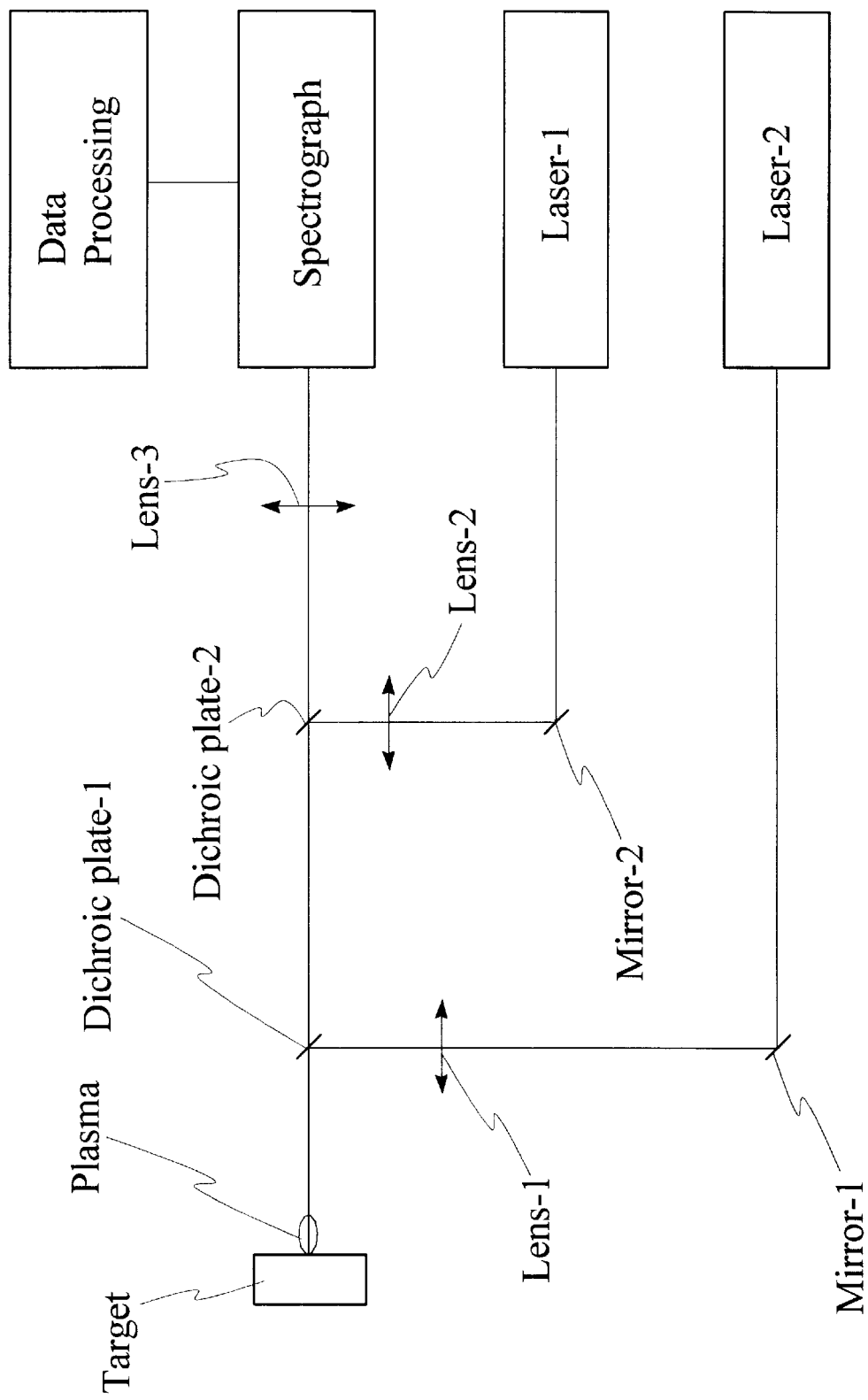
FIG. 1 is an overall block diagram of the apparatus.

The invention uses two high power pulsed laser beams focused on a heterogeneous material, typically two collinear lasers providing two pulses each of the order of 10 nanoseconds in duration and separated typically by about 1 microsecond from each other. The first laser pulse vaporizes a small volume at the surface of the material and produces plasma that is subsequently reheated and enhanced by the second laser pulse. The optical emission of the enhanced plasma is analyzed with a collinear optical spectrometer. The pulsed spectrum is detected through appropriate optics by a gated photodiode array detector, an intensified CCD camera, or by an array of photomultipliers each individually positioned to detect a line emission representative of a given element present in the material.

The material may be opaque or partly transparent. As a result of the high temperature generated, a small amount of the material is ablated, vaporized and ionized, its atoms and ions being in excited states, thus allowing emitting species in the plasma to be identified by spectrally and temporally resolving the spark light emission.

Shortly after the beginning of the laser pulse (say, after 0.1 nanoseconds from the beginning of a laser pulse nearly 10 nanoseconds long) the material vaporized from the target surface is close to the surface and still not significantly ionized. Such highly compressed vapor, not yet a plasma, is expanding rapidly. Subsequently, as more and more of the laser pulse energy produces ionization, the initially transparent matter present in the focal volume becomes an optically opaque plasma, absorbing more and more efficiently the laser beam. As a result, the latter portion of the laser pulse is absorbed by the plasma cloud rather than by the target surface, which is thus shielded from the incoming laser beam, this beam continuing to heat up the plasma while the target surface starts to cool down so that the ablation process substantially drops.

While the plasma absorbs the laser beam power, its temperature increase is mitigated, and later on inverted, because of the thermal losses due to adiabatic expansion, radiation, thermal conduction to the surrounding atmosphere and to the target surface. The thermal conduction loss to the target surface is most important at the beginning of the process when the highly compressed plasma is very close to the surface of the much denser opaque material. As a result, conventional single-pulse plasma emission is limited for several reasons: 1) the amount of material vaporized and injected into the microplasma is limited because of the shielding by the plasma of the incoming laser beam, which substantially shortens the ablation process; 2) the plasma temperature is limited and decays fast because of the high thermal losses; 3) the material may be incompletely atomized, if small lumps of not vaporized matter are brought into the plasma by micro-explosions at the surface of the target (perfect atomization being the necessary preliminary to single atom excitation, ionization and emission); and 4) only a fraction of the plasma material is effectively producing a useful emission spectrum because of the strong temperature gradient within the plasma: when the spectrum is analyzed, typically after a microsecond from the laser pulse, the expanded microplasma comprises a still very hot core, close to the target, which is too hot to give a clear line spectrum and rather provides an interfering spectrally continuous background; a cooler outer portion which no longer emits, and an intermediary region of the proper middle temperature which is the only plasma portion to produce a meaningful line spectrum.

Let us now assume that two colinear laser pulses are used to subsequently bombard the same focal spot on the surface of the analyzed material. The two pulses are temporally spaced by a time period, typically from 0.5 to about 5 microseconds, e.g. of the order of 1 microsecond, which is not long enough to let the plasma spark produced by the first pulse to lose its ionization. The second pulse, produced by a laser whose wavelength is efficiently absorbed by the plasma, is thus absorbed by the portion of the plasma spark which faces the incoming laser beams as well as the collection optics of the analyzing spectrometer, also collinear with the two laser beams. Consequently, the hot portion of the plasma spark produced by the second laser pulse irradiates directly into the spectrometer optics without shading, while thermal conduction losses from the plasma to the surface of the much denser opaque material are minimized. This is because during the period of time between the two pulses the microplasma has had the time to expand away from the target surface. The result is a plasma spark, as produced by the second laser pulse, of high and sustained temperature and emissivity. Furthermore, if the first pulse is generated by a laser whose wavelength is little absorbed by the plasma, substantially all of the first laser pulse energy reaches the target surface without shielding, thus maximizing the mass of the ablated material (the plasma emission level being, obviously, proportional to the mass of radiating material in the plasma). Also, full atomization is reached during the period of time between the two pulses. Finally, due to the flat, homogeneous temperature distribution across the plasma after the second laser pulse, a larger fraction of the plasma material produces a meaningful line spectrum of higher and more sustained intensity. As a result, one can record a plasma emission signal that is orders of magnitude stronger than what would be obtained with a single laser pulse of similar energy.

FIG. 1 shows a schematic diagram of an embodiment of the apparatus of the invention. Two laser beams are aligned colinearly with each other and with the axis of the optical spectrograph by a proper collection of mirrors and dichroic plates. Each of the dichroic plates is chosen so as to effectively reflect most of the respective laser beam wavelength and transmit most of the other wavelengths, so that optical combination losses are minimized. Each of the laser beams is focused on the target surface by an appropriate lens, while a third lens is used to collect the optical emission from the plasma to the entrance of the spectrograph, typically a grating spectrometer equipped with a gated detector such as an intensified photodiode array detector, CCD camera, or an array of photomultipliers each individually positioned in the focal plane, to detect simultaneously and during a specified time period, a number of emission lines representative of different elements in the material to be analyzed. Standard techniques are used to properly synchronize the lasers and detectors so as to collect the emission signal during the time window providing the best signal to noise ratio, while a fast computer evaluates the measured spectra and calculates the element concentrations via calibration procedures which are well known by spectroscopists.

It is known that the plasma absorption due to inverse bremsstrahlung is approximately proportional to the square of the laser wavelength (see, e.g., Hauer A. A. and Bladis H. A. in Laser Induced Plasmas and Applications; Radziemski L. J. and Cremers D. A., Eds. Marcel Dekkert: New York, 1989, Chap. 3). One can thus use a first laser pulse from a short wavelength laser such as an ultraviolet laser, in our case a frequency-quadrupled Nd-YAG laser at 266 nm, to effectively penetrate for a longer period the developing plasma and reach the target surface for maximum laser ablation, while a second pulse from a laser of longer wavelength, such as an infrared laser at 1064 nm in our case, is used to heat up the plasma cloud to obtain a large volume low-density, high-temperature and durable plasma whose enhanced emission is collected by the spectrograph. Another possibility would be e.g. to generate a first laser pulse in the UV and the second pulse in the visible range, or far IR.

Alternatively, the first pulse can be in the visible range and the second in IR; or, the first pulse can be in the short infra-red and the second pulse in the far-IR.

Figure 2:
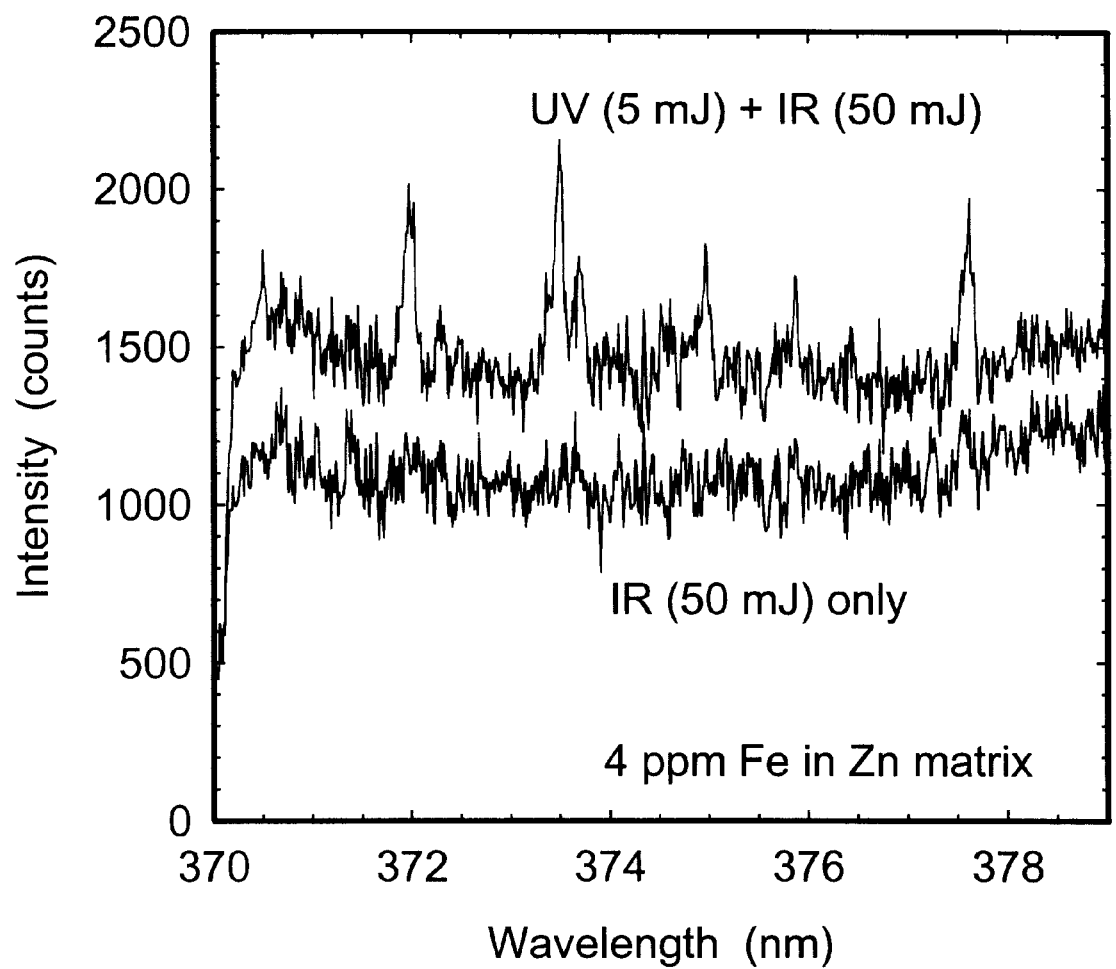
FIG. 2 shows an emission spectrum of plasma produced by 2 sequential pulses separated by 0.5 microseconds, the first pulse in the UV region, 266 nm, and the second in the IR region, 1064 nm, on electrolytic zinc samples and compared to that produced by one single shot at 1064 nm with the combined amount of energy.

An example of two spectra obtained with such an apparatus is shown in FIG. 2. The two spectra were obtained by firing on a 1 mm-diameter spot at the surface of electrolytic zinc metal samples (containing a very low concentration, 4 ppm, of Fe in a Zn matrix) by a single shot of 50 mJ energy from a 1064 nm infrared laser (lower trace) and by a double shot (upper trace). The double shot was obtained by using two colinear lasers, the first giving a 5 mJ pulse in the UV (266 nm), and the second giving a 50 mJ pulse in the IR (1064 nm), the interpulse separation being 0.5 microseconds. Although the total laser energy is almost the same in the two cases, one can see that the Fe lines, such as the one at 372 nm, are very clearly visible in the double-pulse spectrum, while they are completely missing in the single-pulse spectrum. This confirms the effectiveness of the method of the invention, which provides an intense and sustained line emission spectrum even in the case of an extremely low Fe concentration which cannot be detected in the conventional single-pulse approach.

Figure 3:
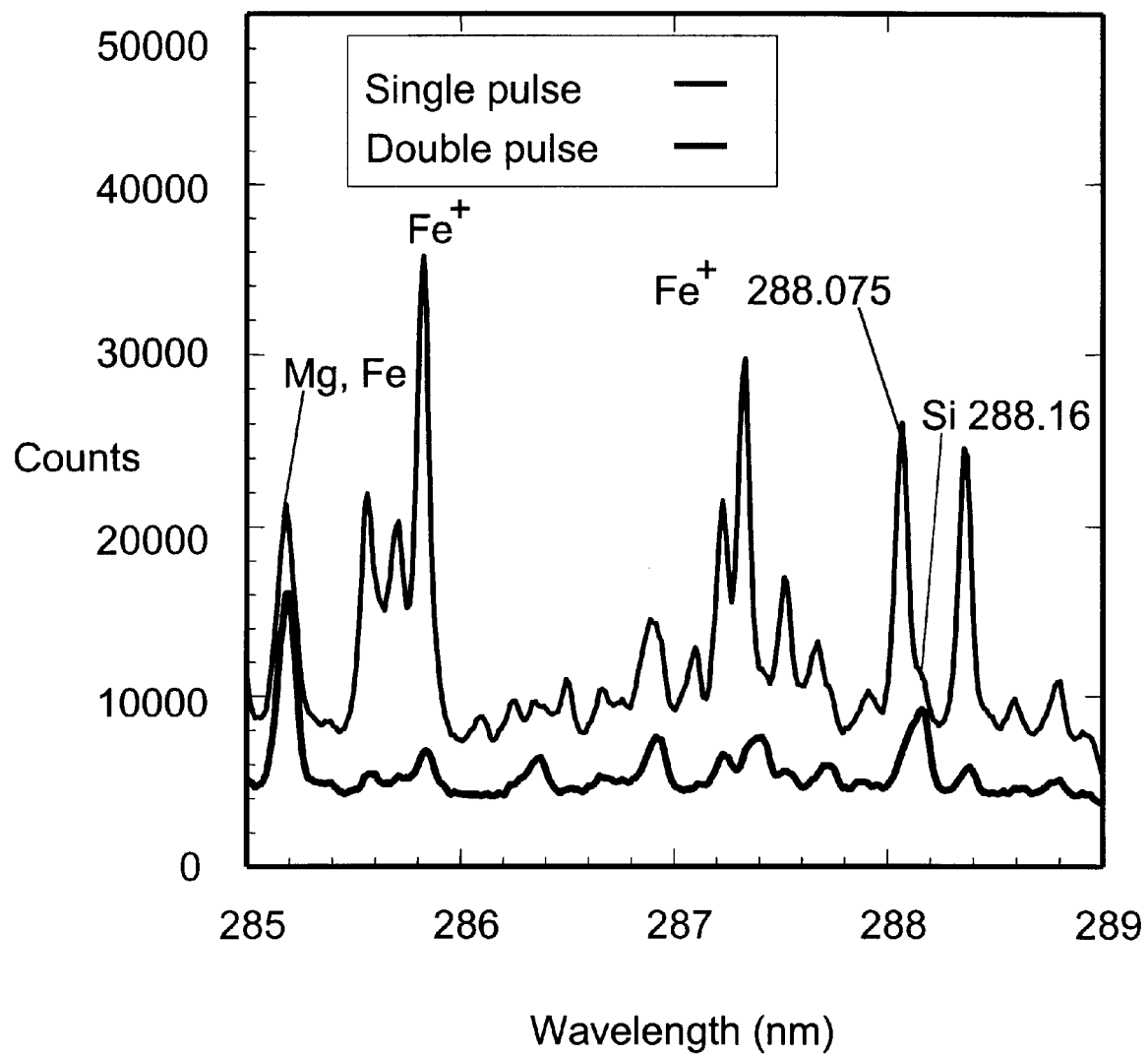
FIG. 3 shows the spectra obtained with a Nd-YAG Q-switched laser focused on an iron ore concentrate slurry showing the silicon line 288.16 nm and several iron lines for one single shot and double pulse (using the same wavelength at 1064 nm). The laser energy was 160 mJ for one single shot and double shot (each one 80 mJ)
Figure 4:
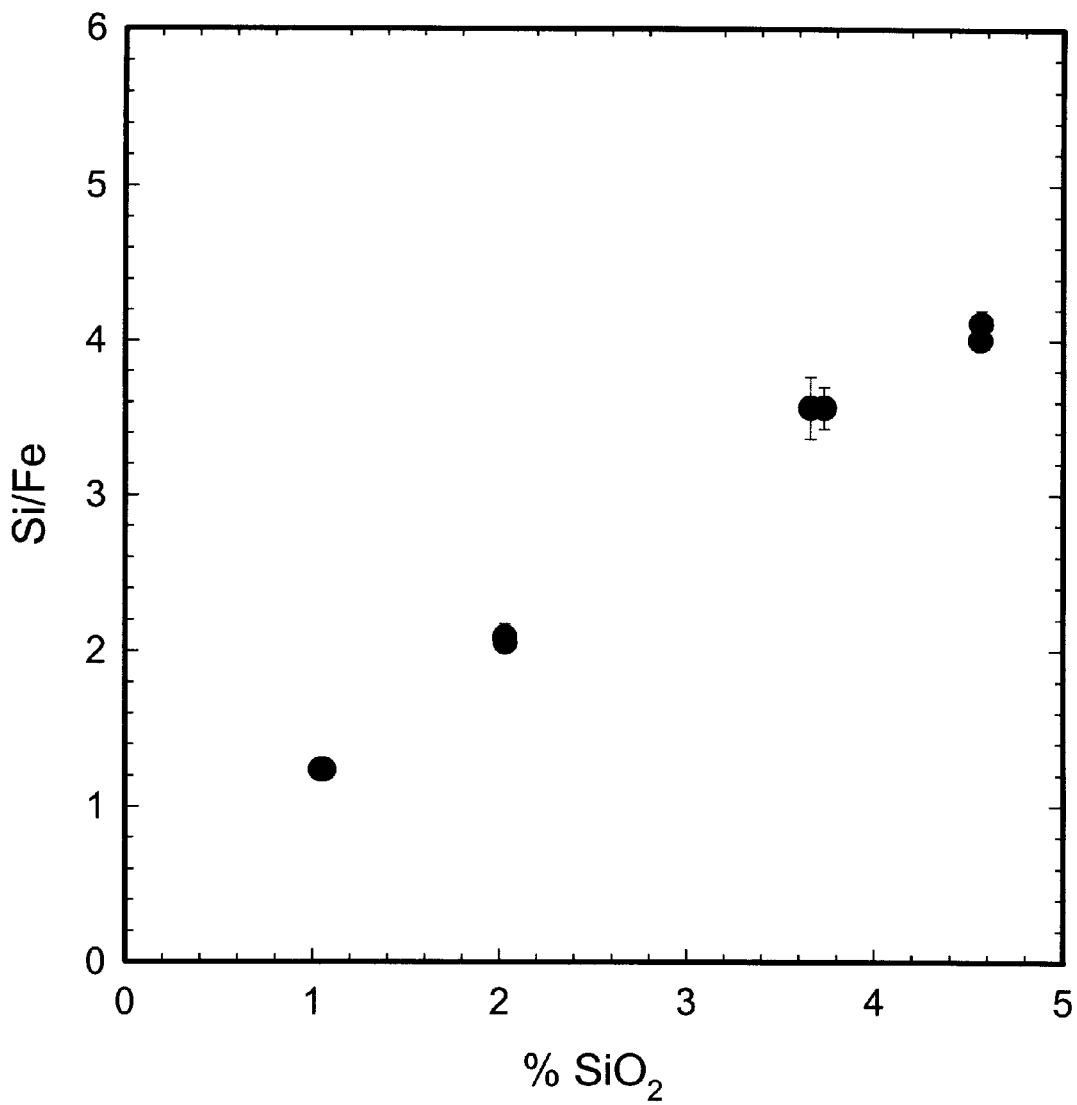
FIG. 4 shows the calibration curve for silica in an iron ore concentrate slurry using double pulses of 160 mJ total energy.

Another example is shown in FIGS. 3 and 4. Here the double pulses are fired on iron ore concentrate slurries. Such slurries are optically opaque, so that the spark still takes place at the surface rather than in the bulk of a transparent liquid as in the above mentioned U.S. Pat. No. 4,925,307, but the penetration of the laser beam below the slurry surface is deeper here than in the case of the metal target described in FIG. 2 (the penetration is probably of a few tens of micrometers in slurries, as compared to less than a micrometer for metals). Consequently, the amount of laser ablation with slurries appears to be acceptable even when using a first shot from an IR laser. It is therefore possible, in the case of a slurry, to use the same laser wavelength, 1064 nm, for both the first and the second shot, so that a single double-fired Nd: YAG laser could be used here thus simplifying the alignment.

The delay between the second pulse and the measurement of the radiation is in the order of microseconds. This delay depends on the energy of the second pulse and the characteristics of the material. The delay can be determined experimentally by the user or can be integrated into the computer system for a specific need.

FIG. 3 shows a comparison of the spectra obtained on iron ore concentrate slurries with a double pulse of 90 mJ for each pulse (lower trace) and with a single pulse of the same total pulse energy, 180 mJ (upper trace).The two pulses were separated by an interpulse period of 0.7 microseconds. The purpose of this analysis was to evaluate the concentration of Si in the iron ore. Because of the predominant concentration of Fe in iron ore, one can see that the Si 288.16 nm line is thwarted by the much stronger 288.075 nm iron ion line in the single-pulse upper trace. Conversely, in the lower double-pulse spectrum the Si line is stronger while the interfering Fe line, which is an ionic line having a higher excitation energy level, is minimized thanks to the more uniform temperature distribution in the double-shot plasma which reduces the background from the hot core present in the single-pulse plasma as described above. The calibration curve obtained with the double-pulse method on iron ore samples containing different Si concentrations is shown in FIG. 4. One can appreciate the good linearity and reliability of this calibration curve obtained with the double-pulse approach. No useful results would have been obtained with the conventional single-pulse approach in this case.

The above description of the present invention is susceptible to various modifications, changes and adaptations, and the same are intended to be comprehended within the meaning of the appended claims.

We claim:

1. A method for spectroscopic analysis of a heterogeneous material, the method comprising:

a) directing a first single high intensity laser pulse at the surface of said material to generate an ionized plasma, b) waiting a time period that is shorter than sufficient for said plasma to lose its ionization, then c) directing a second single high intensity laser pulse at the plasma generated by the first pulse collinearly with said first pulse, said second pulse being of a wavelength substantially longer than the wavelength of said first laser pulse, to enable at least partial absorption of the energy of said second pulse by said plasma and to create an enhanced plasma containing radiation which is representative of a selected component present in said material, d) measuring the intensity of said radiation of said enhanced plasma collinearly with said first laser pulse and said second laser pulse, and e) determining the concentration of said selected component in said material as a function of said intensity of said radiation.

2. The method of claim 1 wherein said predetermined time period is between about 0.1 and about 5 microseconds.

3. The method according to claim 1 wherein the step e) is effected by comparing said intensity of said elemental radiation with a known radiation intensity of said element.

4. The method of claim 3 wherein said comparison is effected using a calibration curve obtained by recording normalized signal levels corresponding to samples with predetermined varying elemental concentrations.

5. The method of claim 1 wherein said first and second pulses are generated by two colinear lasers respectively.

6. The method of claim 1 wherein said first and second pulses are generated by a single laser.

7. The method of claim 1 wherein said first pulse has a wavelength in the UV range and the second pulse has a wavelength in the IR range.

8. The method of claim 1 wherein said first pulse has a wavelength in the UV range and the second pulse has a wavelength in the visible range.

9. The method of claim 1 wherein said first pulse has a wavelength in the visible range and the second pulse has a wavelength in the IR range.

10. The method of claim 1 wherein said first pulse has a wavelength in the near-IR range and the second pulse has a wavelength in the far-IR range.

11. An apparatus for laser-induced spectroscopic analysis of a heterogeneous material, the apparatus comprising:

means for emitting two collinear sequential laser pulses temporally spaced by a predetermined time period, the wavelength of said second pulse being substantially loner than the wavelength of said first pulse, means for focusing a first of said two pulses on the surface of said material to generate a plasma of said material, means for focusing a second of said two pulses on said plasma to generate an enhanced plasma emitting an optical radiation containing radiation which is representative of a selected component of said heterogeneous material, measuring means disposed collinearly with said emitting means for measuring said optical radiation of said enhanced plasma after the second laser pulse, and data processing means for determining the concentration of said component in said material.

12. The apparatus of claim 11 where said emitting means are two effectively colinear lasers.

13. The apparatus of claim 11 where said emitting means is a single laser.

14. The apparatus of claim 11 where said measuring means is an optical spectrometer.

15. The apparatus of claim 14 wherein said spectrometer comprises an enhanced gated photodiode array of detectors.

16. The method of claim 14 where said spectrometer comprises an array of individually positioned photomultipliers.

* * * * *